(12) United States Patent
Yan

(10) Patent No.: US 11,952,492 B2
(45) Date of Patent: Apr. 9, 2024

(54) BIODEGRADABLE, CONTROLLED RELEASE MICROCAPSULES

(71) Applicant: ENCAPSYS, LLC, Appleton, WI (US)

(72) Inventor: Nianxi Yan, Appleton, WI (US)

(73) Assignee: ENCAPSYS, LLC, Appleton, WI (US)

(*) Notice: Subject to any disclaimer, the term of this patent is extended or adjusted under 35 U.S.C. 154(b) by 212 days.

(21) Appl. No.: 17/528,834

(22) Filed: Nov. 17, 2021

(65) Prior Publication Data

US 2022/0162444 A1    May 26, 2022

Related U.S. Application Data

(60) Provisional application No. 63/116,784, filed on Nov. 20, 2020.

(51) Int. Cl.
*C08L 75/06*    (2006.01)
*B01J 13/14*    (2006.01)

(52) U.S. Cl.
CPC ............... *C08L 75/06* (2013.01); *B01J 13/14* (2013.01); *C08L 2201/06* (2013.01); *C08L 2207/53* (2013.01)

(58) Field of Classification Search
None
See application file for complete search history.

(56) References Cited

U.S. PATENT DOCUMENTS

| | | | |
|---|---|---|---|
| 2002/0009599 A1 | 1/2002 | Welch et al. | |
| 2010/0303850 A1* | 12/2010 | Lipford | A61P 43/00 424/193.1 |
| 2011/0045975 A1* | 2/2011 | Ehr | A01N 25/28 504/105 |
| 2013/0337023 A1 | 12/2013 | Lei et al. | |
| 2015/0087517 A1 | 3/2015 | Verheesen et al. | |

FOREIGN PATENT DOCUMENTS

| | | |
|---|---|---|
| WO | 1994013139 | 6/1994 |
| WO | 2017089115 W2 | 6/2017 |
| WO | 2018002214 A1 | 1/2018 |
| WO | 2020209909 4 | 10/2020 |

OTHER PUBLICATIONS

Hoppe et al., Identification and quantification of oligomers as potential migrants in plastics food contact materials with a focus in polycondensates e A review (Year: 2016).*
International Search Report and Written Opinion for PCT/US2021/059932, Int'l PCT equivalent to instant application, dated Feb. 17, 2022.
Gelita Sol C Brouchure, Gelita AG, 2014.
Gelita RXL Portfolio Brouchure, Gelita AG, 2016.
Modern Technologies for Innovative Production: The Production of Gelatine, Gelita AG.
Kidchob, T, et al., "Preparation, structure and release profile of polypeptide microcapsules", J. Controlled Release, 40, 285-291, 1996.

* cited by examiner

*Primary Examiner* — Jeffrey D Washville
(74) *Attorney, Agent, or Firm* — Hoffmann & Baron, LLP; Edward K Welch, II

(57) ABSTRACT

Controlled release biodegrading microcapsules comprising polypeptide chains.

22 Claims, 1 Drawing Sheet

BIODEGRADABLE, CONTROLLED RELEASE MICROCAPSULES

The present disclosure relates to biodegradable, controlled release microcapsules whose microcapsule walls comprise the reaction product of peptides with and isocyanates and/or bis- or poly-chloroformates. In particular and preferably the microcapsule walls are formed from polypeptides and isocyanates wherein all or a majority of the isocyanates have at least two isocyanate groups.

BACKGROUND

Microcapsules and microencapsulation technology are old and well known and their commercial applications varied. Microcapsules have played a significant role in various print technologies where a paper or other like substrate is coated with microcapsules containing ink or an ink-forming or inducing ingredient which microcapsules release the ingredient, generating an image, when fractured by pressure, as by a printing press or a stylus. Microcapsules have also played a significant role in various adhesive and sealant technologies including the encapsulation of solvents for solvent swellable/tackified preapplied adhesives whereby fracture of the microcapsules releases the solvent which softens or tackifies the adhesive to enable bonding and which re-hardened upon evaporation of the solvent. In other adhesive and sealant applications, the microcapsules contain one or more components of a curable or polymerizable adhesive or sealant composition which, upon release, leads to the cure or polymerization of the adhesive or sealant. In all of these early applications, functionality and efficacy, especially for long term storage and utility, is dependent upon the integrity of the microcapsule walls where the sought-after integrity pertains to both strengths, so as to avoid premature fracture, as well as impermeability, so as to prevent leakage and/or passage of the contents of the microcapsule through the microcapsule walls. In the former situation, parts having a preapplied microencapsulated adhesive have a tendency to bond together if they hit one another or are stacked upon one another where the pressure of the stack is sufficiently high. Even if not bonded, the fracture of the microcapsules results in less adhesive to effect the bond when the bond is intended. Similarly, if the microcapsule walls allow permeation of the active components through the cell wall, even a slow permeation, the product is short lived as cure will be effected when not intended.

As with most any technology, evolution of microencapsulation technology has led to many new applications, including applications that require changes in the physical properties of the microcapsules, especially their walls. New applications require microcapsules that fracture more readily, with less pressure, but not prematurely. Other applications require microcapsules that specifically allow for a controlled, slow release or permeation of the contents from within the microcapsules without the need to actually fracture the same. For example, perfume containing microcapsules are oftentimes applied to advertising inserts in magazines so that the reader can sample the smell of the perfume. Here strength is needed to avoid premature fracturing of the microcapsules due to the weight and handling of the magazine; yet, the microcapsules need ease of fracture so that the reader can simply scratch the treated area to release the contents of the microcapsule. At the same time, it is desirable to allow for some release of the contents, even without fracturing, to induce the reader to want to scratch the sample to get a more accurate sense of the smell.

Another application for microcapsules is in laundering and fabric treatments. A number of products exist wherein microcapsules of various ingredients, including perfumes, are applied to strips of a fabric material and added to the dryer wherein the tumbling action and/or heat of the dryer causes the microcapsules to fracture, releasing the ingredients which, in a volatilized state, permeate and deposit upon the contents of the dryer. This methodology applies that "fresh out of the dryer" smell, but is short lived as the perfume continues to volatilize from the treated fabric. Other products exist whereby microcapsules containing perfumes and other ingredients are applied directly or indirectly to the fabric, especially apparel, to provide a longer-lived freshness to the same. Here, the performance or efficacy of these products is oftentimes short lived as the content of the microcapsules escapes too readily from the microcapsules and/or the walls of the microcapsules are too weak and/or have too little give such that normal wearing of the fabric causes the microcapsules to break too readily.

Whether applications have driven the evolution of microcapsule technology or the evolution of microcapsule technology has driven their expanded applications, or perhaps a little of both, there has been and continues to be constant development in microencapsulation technology, both in terms of their production/process methodology and their chemistry. Early melamine formaldehyde microcapsules continue to evolve; yet concurrently, they have, to some extent, given way to acrylic and other microcapsule chemistries and technologies. In turn, both have continued to evolve further to dual walled microcapsules of each chemistry as well as both chemistries. While the basic building blocks of the capsule walls have largely remained the same, the specific selection of building blocks and methodology has led to newer and improved microcapsules enabling the microencapsulation of a broader array of ingredients, compounds and elements.

With all the advances and improvements noted and the continued expansion of microcapsule use for a myriad of applications, there is a growing buildup of microcapsules in the environment and, in following, in animal species feeding on materials containing and/or contaminated with microcapsules. Unfortunately, these microcapsules are formed of synthetic polymeric materials and remain in the environment for decades, if not centuries. Although not yet required by various governmental/regulatory agencies, movement is afoot to control the use of such polymeric microcapsules.

According there is a growing and, some may say, an urgent need for microcapsules whose walls are biodegradable. While capsules and, in some instances, microcapsules whose walls are formed of gelatin, albumin, polylactide and poly(lactide-co-glycolide), all generally considered biodegradable materials, have been tested, particularly for use in the pharmaceutical and nutritional supplement industries, these materials are and their characteristics make them difficult to use, particularly in the production of microcapsules. Additionally, the resultant microcapsules are lacking in their physical properties and performance as compared to traditional, generally non-biodegradable, microcapsules. Microcapsules have also been formed of block polypeptides; however, again their properties and performance are limited: certainly not appropriate for the myriad of commercial applications of traditional microcapsules. Additionally, their method of production, solvent evaporation, is not suitable for commercial large-scale production, let alone, encapsulation of the breadth of materials capable of being microencapsulated by more conventional microencapsulation techniques.

Accordingly, there is continuing need and growing urgency for microcapsules that are biodegradable yet retain, at least for the most part, the beneficial properties, release control and breadth of utility of current traditional microcapsules.

In following there is a continuing need and growing urgency for microcapsules that are biodegradable and allow for a controlled release of their contents.

SUMMARY

According to the present teachings there are provided novel microcapsules and methods of forming the same, whose microcapsule walls comprise the reaction product of peptides with isocyanates and/or bis- or poly-chloroformates. In particular, there are provided novel microcapsules whose walls comprise the reaction product of isocyanates, wherein all or the majority of the isocyanate is a di- or higher isocyanate, including aromatic, aliphatic and combinations thereof, and peptides, more appropriately, polypeptides, having at least two sites reactive with the isocyanates, wherein the peptide has an average molecular weight (Da) of less than 10,000, preferably 7,000 or less, most preferably 5500 or less. Similarly, the peptides have an average molecular weight of at least 375, preferably at least 600, more preferably at least 1000, most preferably at least 1700. Preferred polypeptides comprise from 5 to 50, preferably 15-45, most preferably 20-40 amino acids. Where the isocyanate component includes mono-functional isocyanate, at least 50% by weight, preferably at least 70%, more preferably at least 80% by weight, most preferably at least 90% by weight of the isocyanate is a di- or higher isocyanate. Property and performance characteristics of the microcapsules can be controlled by selection of the peptides, the isocyanate and/or bis- or poly-chloroformate, the microencapsulation process employed and the weight ratio of isocyanate and/or bis- or poly-chloroformate to peptide. Typically, the weight ratio of the former, particularly the isocyanate, to peptide is from 100:1 to 1:100, preferably from 50:1 to 1:50, more preferably 10:1 to 1:10. While such higher ratios are suitable, it is especially preferred that the weight ratio of the former to peptide be from 1:5 to 1:0.2, preferably 1:4 to 1:0.5, more preferably 1:2 to 1:1.

The microencapsulation process of the present teaching is employed to provide carrier microcapsules containing various core materials including solids, hydrophilic agents, hydrophobic agents, lipophilic agents and the like, especially UV absorbers, UV reflectors, pigments, dyes, colorants, scale inhibitors, corrosion inhibitors, antioxidants, pour point depressants, waxes, deposition inhibitors, dispersants, flame retardants, biocides, active dye tracer materials, odor control agents, natural oils, flavor and perfumes oils, crop protection agents, pharmaceuticals, medicaments, phase change materials and the like.

DETAILED DESCRIPTION

Figure 1:
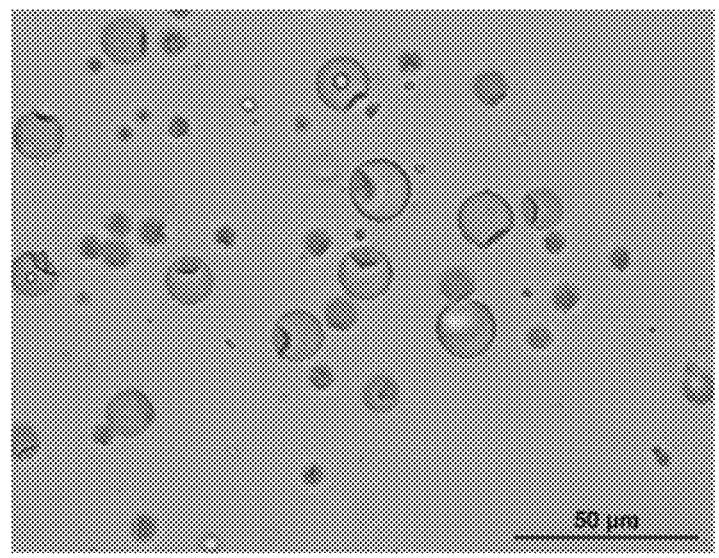
FIG. 1 is a photomicrograph of the microcapsules prepared according to the present teaching.

The present teaching is directed to novel microcapsules and the process by which they are made. In particular, the present teaching is directed to microcapsules that are biodegradable and server as carriers for various core materials contained therein including solids, hydrophilic agents, hydrophobic agents, lipophilic agents and the like. Most especially, the present teaching is directed carrier microcapsules that are biodegradable and have controlled release properties for the liquid/volatile core materials contained therein.

The microcapsules according to the present teaching are unique in that their walls comprise polyurethanes, polyureas and/or polyurethane-ureas formed by the reaction of i) (a) isocyanates, especially diisocyanate and/or polyisocyanates and/or (b) bis- or poly-chloroformates, and ii) peptides, specifically polypeptides, having at least two sites reactive with the isocyanates and/or chloroformates and having an average molecular weight (Da) of less than 10,000, preferably 7,000 or less, most preferably 5500 or less. Similarly, the peptides have an average molecular weight of at least 375, preferably at least 600, more preferably at least 1000, most preferably at least 1700. Preferred polypeptides comprise from 5 to 50, preferably 15-45, most preferably 20-40 amino acids. Reactive sites on the peptides are preferably primary amino reactive sites, though secondary amino and hydroxyl groups may also be present: most preferably all or significantly all of the reactive sites are primary amino reactive sites.

Similarly, the process by which the present microcapsules are prepared is unique in that it calls for the use of both isocyanates and/or bis- or poly-chloroformates and peptides as the wall forming materials. The microencapsulation process may be a water-in-oil process, an oil-in-water process or a water-in-oil-in water process: the latter process is especially useful when the core material is hydrophilic or water soluble/dispersible; yet one wants to avoid the use of large volumes of oil phase materials as is required of the water-in-oil process. For convenience, the following description is presented in terms of the oil-in-water process: though those skilled in the art will readily appreciate and acknowledge the adaptability of the process to a water-in-oil and water-in-oil-in-water process.

Suitable diisocyanate and polyisocyanates for use in the practice of the present teaching include those known for use in the formation of polyurethane, polyurea, and polyurethane-urea microcapsules and are well known to those of ordinary skill in the art. These isocyanates include aliphatic, cycloaliphatic, aromatic, polyaromatic, etc., isocyanates as well as combinations thereof. Such isocyanates typically have from 2 to 16, preferably 4 to 10 carbon atoms in the basic hydrocarbon skeleton. While the diisocyanates are preferred, polyisocyanates, especially those having 3 or 4 cyanato (NCO) groups, 3 to 10 cyanato groups in the case of dimers and oligomers, as well as combinations of diisocyanates and polyisocyanates are also desirable and useful. While a single isocyanate is suitable, it is also desirable to employ combinations of isocyanate, e.g., a combination of di- and/or poly-isocyanates, a combination of aliphatic and aromatic isocyanates as well as combinations of both. In this regard, the weight percent of each isocyanate may be from 0-100% of the combination. In the case of combinations of aliphatic and aromatic isocyanates, it is preferred that each be present in an amount of at least 5% by weight, preferably at least 10% by weight, more preferably at least 20% by weight, depending upon the desired leakage rate. For example, aliphatic/aromatic isocyanate microcapsules with lower leakage will typically have at least 50% by weight, more preferably at least 70% by weight of the aliphatic isocyanate. Further, while mono-isocyanates may be present, the di- or higher isocyanates comprise at least 50% by weight, preferably at least 70%, more preferably at least 80% by weight, most preferably at least 90% by weight of the isocyanate component.

Exemplary aliphatic and cycloaliphatic isocyanates include 2,2,4-trimethylhexamethylene diisocyanate, 2,4,4-trimethylhexamethylene diisocyanate, 1,4-tetramethylene diisocyanate, 1,6-hexamethylene diisocyanate (HDI), isophorone diisocyanate IPDI), 4,4'-methylene-bis-(cyclohexane diisocyanate), cylcohexane-1,4-diisocyanate, and adducts, trimers, biurets, symmetric trimers, asymmetric trimers thereof, especially of hexamethylene diisocyanate, and the like, including trimethyol propane adducts of hexamethylene diisocyanate.

Aromatic isocyanates include m- and p-tetramethylxylene diisocyanate (TMXDI), α,α'-xylylene diisocyanate, methylene diisocyanate (MDI), especially 4,4'-diphenylmethane diisocyanate, toluene diisocyanate (TDI), 1,4-phenylene diisocyanate, 1,3-phenylene diisocyanate, 2,4,6-triisocyanate toluene, 4,4',4'-triisocyanate triphenyl methane, 1,2,4-benzene triisocyanate, 2,5-norbornene diisocyanate, 3,3'-dimethyldiphenyl-4,4'-diisocyanate, naphthalene diisocyanate, and adducts, trimers, biurets, symmetric trimers, asymmetric trimers thereof, especially of toluene diisocyanate and methylene diisocyanate, and the like. Exemplary trimers include, but are not limited to, the trimer of hexamethylene diisocyanate sold under the trademark Desmodur® N-3390 by Bayer Corporation of Pittsburgh, Pa. and the trimer of isophorone diisocyanate.

Suitable isocyanates also include oligomeric and low molecular weight polymeric isocyanates: again, materials that are well known to those of ordinary skill in the art. Preferably, in keeping with the desirability of degradability, such oligomeric and low molecular weight polymeric isocyanates are formed of an isocyanate and low molecular weight polyols, preferably $C_1$ to $C_6$ polyols, especially diols and/or triols, most especially linear diols and triols. Alternatively, or in additional thereto, consistent with the teaching of the present specification, such oligomeric and low molecular weight polymeric isocyanates may be prepared by the reaction of individual amino acids or lower peptides, 2 to 5 amino acids with isocyanates. In either instance, in the preparation of such oligomers and low molecular weight polymers, an excess of the isocyanate is employed to provide oligomers and low molecular weight polymers with at least two free cyanate groups. Exemplary oligomeric and low molecular weight polymeric isocyanates include, but are not limited to, trimethylol propane adducts of the isocyanates, especially those of toluene diisocyanate, methylene diisocyanate, and xylylene diisocyanate.

Alternatively or in addition to the isocyanates, one may employ bis- and/or poly-chloroformates as the co-reactant with the peptides to form the polyurethane microcapsules. Such chloroformates are well known and widely available as well and generally have the structure ClCO-U-OCCl wherein the U is hydrocarbyl, e.g., alkylidene, or an oxygen containing hydrocarbyl linking group, e.g., diethylene glycol bis chloroformate. Exemplary bischloroformates include monoethylene glycol bis-(chloroformate), diethylene glycol bis(chloroformate), butanediol bis(chloroformate), hexanediol bis(chloroformate), neopentyldiol bis(chloroformate), bisphenol A bis(chloroformate) and mixtures thereof.

Suitable peptides for use in the practice of the present teaching are polypeptides having at least two sites reactive with the isocyanates and/or chloroformates and having an average molecular weight (Da) of less than 10,000, preferably 7,000 or less, most preferably 5500 or less. Preferred polypeptides comprise linear chains of from 5 to 50, preferably 15-45, most preferably 20-40 amino acids, typically, though not exclusively, bonded to one another through a peptide bond. Other bonds may be present in the linear chain including disulfide bonds, sulfur links, urea bonds and the like: though such other bonds will be few in number per peptide chain, typically less than 20%, preferably less than 10%, of the bonds in the peptide chain. As noted, the reactive sites on the peptides are preferably primary amino reactive sites, though secondary amino and hydroxyl groups may also be present: most preferably all or significantly all of the reactive sites are primary amino reactive sites.

The peptides may be derived from natural sources or they may be synthetic, especially those formed by the solid phase peptide synthesis (SPPS) of amino acids. While the most common amino acids have the amine group on the alpha carbon atom along with the carboxyl moiety, the present teaching is not limited to peptides of those amino acids and it is understood that those peptides formed of amino acids wherein the amino group is on the beta or gamma carbon atom and, to a lesser extent, the delta carbon atom are also contemplated and desirable. Most especially the peptides are formed of the alpha and beta amino acids and combinations thereof, most especially the alpha amino acids. Additionally, it is to be appreciated that the amino acids are not limited to those that have a single amine and a single carboxyl group. Rather, suitable amino acids also have a plurality of either or both, e.g., two amine groups and/or two carboxyl groups, as well as other reactive moieties/sites including, for example, the presence of sulfur containing groups or moieties in or on their side chain: the latter providing disulfide links or sulfur bridges. Amino acids are well known, numbering in the hundreds, though the present teaching is especially directed to, but not limited to, peptides formed of the more common and abundant amino acids, as described in greater detail below and as will be appreciated by those skilled in the art.

While the natural peptides are, for the most part, derived from proteinogenic amino acids (they may also contain low levels of non-proteinogenic amino acids), synthetic peptides may be derived from proteinogenic amino acids, non-proteinogenic amino acids and combinations of both, especially, for example, those peptides comprising both the L- and D-isomers of the same or different amino acids. Proteinogenic amino acids are the L-α-amino acids including the L isomers of arginine, histidine, lysine, aspartic acid, glutamic acid, serine, threonine, asparagine, glutamine, cysteine, selenocysteine, glycine, proline, alanine, isoleucine, leucine, methionine, phenylalanine, tryptophan, tyrosine, valine and pyrrolysine. Non-proteinogenic amino acids include the D isomers of the foregoing as well as, for example, but not limited to, α-amino butyric acid, norvaline, norleucine, alloisoleucine, t-leucine, α-amino-n-heptanoic acid, pipecolic acid, α, β-diaminoproprionic acid, α, γ-diaminobutyric acid, ornithine, allothreonine, β-alanine, β-aminobutyric acid, α-aminoisobutyric acid, isovaline, sarcosine, N-ethylglycine, N-propylglycine, N-isopropylglycine, N-methylalanine, N-ethylalanine, N-methyl-β-alanine, N-ethyl-β-alanine, isoserine, α-hydroxy-γ-aminobutyric acid, ornithine, phenylalanine, β-aminobutyric acid, and the like. Of course, the peptides may also be formed of the salts of the amino acids, especially the monohydrochloride salts, including, for example, D-lysine monohydrochloride, L-lysine monohydrochloride, L-arginine monohydrochloride, D-arginine monohydrochloride, L-orthinine monohydrochloride, D-monohydrochloride, and the like.

The peptides used in the practice of the present teaching may also be formed of lower peptides, generally those having 10 or fewer amino acids, preferably 2-5 amino acids, especially dipeptides, tripeptides, and tetrapeptides. Exemplary lower peptides include, but are not limited to the doublet amino acids, such as dialanine, dilysine, diglycine, etc. as well as dipeptides that have other than a peptide bond, including, for example, cystine, cystathionine, ianothianine, djenkolic acid, and diaminopimelic acid, among others.

As noted, the peptides may be homopeptides, wherein the peptide is comprised of the same amino acid, and copeptides, where the peptide is comprised of two or more different amino acids and/or lower peptides, as well as combinations of the two. The copeptides include those peptides wherein the peptide comprises both the L- and D-isomers of the same amino acid. Copeptides also include those peptides having a plurality of amino acids and/or doublet amino acids and/or lower peptides randomly linked along the peptide chain or in a structured arrangement, i.e., block peptides, wherein blocks of low to moderate molecular weight peptides, which may be homopeptides or copeptides, are bonded to one another to make up the full peptide. Such block peptides may be random copeptides, e.g. A-B-A-C-B-A or structured, e.g., A-A-A-C-C-C-B-B-A-A-A, the latter being formed by known techniques such as the sequential polymerization of the low to moderate molecular weight peptide blocks, wherein A, B and C represent low to moderate molecular weight peptides, i.e., oligopeptides of 2 to 30 amino acids, preferably 3-20 amino acids, more preferably 5 to 10 amino acids.

Also contemplated are peptides wherein one or both ends of the peptide chain are terminated with a select amino acid. For example, it may be desirable to have amine or hydroxyl functionality at or near both ends of the peptide chain. The former allowing for polyurea microcapsule wall formation and the latter for polyurethane microcapsule wall formation.

The specific peptides chosen for any given microencapsulation depends upon a number of factors including the desired physical properties, release properties, the particular microencapsulation process to be employed, which phase the peptide is to be introduced into, etc. The selection of amino acids and their numbers play an important role in the physical properties and release properties of the microcapsule walls. Similarly, the selection of amino acids and their percentage make-up of the peptides also greatly affects their solubility/dispersibility in the phase in which it is introduced into the process as well as its affinity or aversion to the other phase. In this respect, it is well appreciated that certain amino acids have polar and/or electrically charged side chains, hydrophobic side chains and the like. Hence, by selection of the amino acids and their concentrations, one can tailor the peptide for their specific need and process. Of course, one may also employ surfactants and other solubilizing/dispersing aids to assist with the solubilization and/or dispersion of the peptides in the select phase. Suitable surfactants and aids include polyvinyl alcohol (PVA), polystyrene sulfonate (PSS), carboxymethylcellulose (CMC), sodium salt of naphthalene sulfonate condensate, and the like, as well as mixtures thereof.

Core materials that may be encapsulated in accordance with the present teaching include a myriad of substances, consistent with those materials that are encapsulated by existing technologies and chemistries. Core materials include solid particles, semi-solid materials, hydrophilic liquids, lipophilic liquids, hydrophobic liquids and the like. Specific selection depends upon the intended utility of the microcapsules. Indeed, microcapsules have a myriad of applications across various industries and consumer products including, but not limited to, agrochemicals, pharmaceuticals, cosmetics industry, personal care products, laundering detergents, homecare & cleaning products, oral care, dental care, textiles, paper, mining, oil industry, water treatment, adhesives, coatings, coatings, plastics, sealants, construction, paints, inks and dye formulations. Exemplary core materials include, but are not limited to UV reflectors, UV absorbers, pigments, dyes, colorants, scale inhibitors, emollient oils, insecticides, detergents, printing inks, corrosion and rust, recording materials, inhibitors, antioxidants, pour point depressants, catalysts, initiators, waxes, deposition inhibitors, dispersants, flame retardants, biocides, active dye tracer materials, silicone conditioners, shampoos, biocides, adhesives, anti-fouling agents, odor control agents, cosmetic additives, oxidizing agents, personal care actives, agrochemicals, fertilizers, fats, nutrients, enzymes, liquid crystals, natural oils, fragrances, flavor and perfume oils, crop protection agents, medicaments, pharmaceuticals, phase change materials and the like. Specific examples of core materials are disclosed in, e.g., US 2013/0337023, U.S. Pat. Nos. 10,456,766, 8,119,214, 9,714,397, 10,485,739, 4,977,060, 10,675,277, US20070138673, and US20130302392, all of which are hereby incorporated by reference, among a myriad of other patents, patent publications and the like.

The following presents a non-limiting list of exemplary core materials.

Linear or branched hydrocarbons of different chain lengths and viscosities such as mineral oil, petrolatum, white oil (also known as paraffin oil), dodecane, isododecane, squalane, hydrogenated polyisobutylene, polybutene, polydecene, docosane, hexadecane, isohexadecane and other isoparaffins, which are branched hydrocarbons.

Alcohol, diol, triol or polyol esters of carboxylic or dicarboxylic acids, of either natural or synthetic origin having straight chain, branched chain and aryl carboxylic acids include diisopropyl sebacate, diisopropyl adipate, isopropyl myristate, isopropyl palmitate, myristyl propionate, cetyl lactate, myristyl lactate, lauryl lactate, C12-15 alkyl lactate, dioctyl malate, decyl oleate, isodecyl oleate, ethylene glycol distearate, ethylhexyl palmitate (octyl palmitate), isodecyl neopentanoate, tridecyl neopentanoate, castoryl maleate, isostearyl neopentanoate, di-2-ethylhexyl maleate, cetyl palmitate, myristyl myristate, stearyl stearate, cetyl stearate, isocetyl stearate, dioctyl maleate, octyl dodecyl stearate, isocetyl stearoyl stearate, octyldodecyl stearoyl stearate dioctyl sebacate, diisopropyl adipate, cetyl octanoate, glyceryl dilaurate, diisopropyl dilinoleate and caprylic/capric triglyceride. Naturally occurring includes triglycerides, diglycerides, monoglycerides, long chain wax esters and blends of these. Examples of naturally derived ester-based oils and waxes include, but are not limited to, argan oil, corn oil, castor oil, coconut oil, cottonseed oil, menhaden oil, avocado oil, beeswax, carnauba wax, cocoa butter, palm kernel oil, palm oil, peanut oil, shea butter, jojoba oil, soybean oil, rapeseed oil, linseed oil, rice bran oil, pine oil, sesame oil, sunflower seed oil and safflower oil. Also useful are hydrogenated, ethoxylated, propoxylated and maleated derivatives of these materials, e.g., hydrogenated safflower oil, hydrogenated castor oil. Cholesterol and its esters and derivatives, as well as natural materials comprising cholesterol derivatives such as lanolin and lanolin oil.

Phospholipids (e.g., lecithin), sphingophospholipids, ceramides and related materials.

C4-C20 alkyl ethers of polypropylene glycols, C1-C20 carboxylic acid esters of polypropylene glycols, and di-C8-C30 alkyl ethers. Also included are PPG-14 butyl ether, PPG-15 stearyl ether, diodyl ether, dodecyl octyl ether, and mixtures thereof.

Saturated and unsaturated fatty acids including but not limited to oleic, palmitic, isostearic, stearic, ricinoleic, linoleic and linolenic acid. Carboxylic monoesters and polyesters of sugars (mono-, di- and polysaccharides) and related materials.

Silicones such as polyalkylsiloxanes, polydialkylsiloxanes, polydiarylsiloxanes, and polyalkarylsiloxanes may also be used. This includes the polydimethylsiloxanes, which are commonly known as dimethicones. Further cyclic siloxanes (e.g., cyclopentasiloxane) and dimethiconoles, alkyl methicones, alkyl dimethicones, dimethicone copolyols, amino-functional silicones (e.g., amodimethicone, trimethylsilyloxyamodimethicone) and amphoteric silicones (e.g., cetyl PEG/PPG-15/15 butyl ether dimethicone, and bis-PEG-18 methyl ether dimethyl silane).

Oily and oil-soluble extracts of plant materials such as flowers and herbs. This comprises a wide range of materials, with some non-limiting examples including extracts of rosemary, green, white or black tea, orchid, grape seed, sage, soybean, Echinacea, Arnica, rosehip, olive, artichoke. Further plant-extracted oil-soluble components such as lycopene and other mixed carotenoids, capsaicin and capsaicinoids, polyphenols (e.g., rosmarinic acid), terpenes and terpenoids, oleoresins.

Exemplary dyes include, but are not limited to, Green 6 (CI 61570), Red 17 (CI 26100), Violet 2 (CI 60725) and Yellow 11 (CI 47000). Examples of oil-dispersible pigments include, but are not limited to Beta Carotene (CI 40800), Chromium Hydroxide Green (CI 77289), Chromium Oxide Green (CI 77288), Ferric Ferrocyanide (CI 77510), Iron Oxides (CI 77491, 77492 77499), Pigment Blue 15 (CI74160), Pigment Green 7 (CI 74260), Pigment Red 5 (CI 12490), Red 30 (CI 73360), Titanium Dioxide (CI 77891) and Ultramarines (CI 77007).

Exemplary pharmaceutical active, especially for dermatological treatment of conditions of skin, hair and nails include, but is not limited to, topical anaesthetics, antifungal, anti-bacterial, anti-viral, anti-dandruff, anti-acne and anti-inflammatory agents (steroidal and non-steroidal).

Examples of vitamin and derivatives include tocopherol, tocopheryl acetate, retinol, retinyl palmitate, ascorbyl palmitate, niacinamide, beta carotene.

The fragrances suitable for use in this invention include without limitation, any combination of perfumes, flavors, essential oils, sensates and plant extract or mixture thereof that is capable of being encapsulated in accordance with the present application. A list of suitable fragrances is provided in U.S. Pat. Nos. 4,534,891, 5,112,688, 5,145,842, 6,194,375, 20110020416 and PCT application Nos. WO2009153695 and WO2010/044834 and Perfumes Cosmetics and Soaps, Second Edition, edited by W. A. Poucher, 1959. Each of the foregoing documents is incorporated herein by reference in its entirety.

Typical representative perfume and sensate components include, but are not limited to, linalool, coumarin, geraniol, citral, limonene, citronellol, eugenol, cinnamal, cinnamyl alcohol, benzyl salicylate, menthol, menthyl lactate, eucalyptol, thymol, methyl salicylate, methylfuran, menthone, cinnamaldehyde.

Typical representative examples for essential oils include, but are not limited to, orange, lavender, peppermint, lemon, pine, rosemary, rose, jasmine, tea tree, lemon grass, bergamot, basil, spearmint, juniper, clove, aniseed, fennel, cypress, fir, black pepper, sandalwood, cedarwood, rosewood, cardamom, cinnamon, coriander, Eucalyptus, geranium, ginger, chamomile, grapefruit, neroli, petitgrain, thyme, vetiver and ylang ylang.

Non-limiting examples of phase change materials include n-octacosane, n-heptacosane, n-hexacosane, n-pentacosane n-tetracosane, n-tricosane, n-docosane, n-heneicosane, n-eicosane, n-nonadecane, n-octadecane, n-heptadecane, n-hexadecane, n-pentadecane, n-tetradecane and n-tridecane.

Chemical and physical sunscreens/UV filters, e.g., 3-Benzylidene Camphor, 4-Methylbenzylidene camphor, Aminobenzoic acid (PABA)' Avobenzone, Benzophenone 4 (Sulisobenzone), Benzophenone 5, Benzophenone 8, Benzophenone-3, Benzylidene camphor sulfonic acid, Bisethylhexyloxyphenol methoxyphenol triazine (Escalol S), Butyl methoxy dibenzoylmethane, Camphor benzalkonium methosulfate, Cinoxate, Diethylamino hydroxybenzoyl hexyl benzoate, Dioxybenzone, Disodium phenyl dibenzimidazole tetrasulfonate, Drometrizole trisiloxane, Ensulizole, Ethylhexyl dimethyl PABA, Ethylhexyl methoxycinnamate, Ethylhexyl salicylate, Ethylhexyl triazone, Homosalate, Isoamyl p-methoxycinnamate, Meradimate, Menthyl anthranilate, Methylene bis-benzotriazolyltetramethylbutylphenol/Bisoctrizole (Tinosorb M), Octocrylene, Octinoxate, PEG-25 PABA, Octisalate, Oxybenzone, Padimate O, Phenylbenzimidazole sulfonic acid, Polyacrylamidomethyl Benzylidene Camphor, Polysilicone-15, TEA-salicylate, Terephthalylidene dicamphor sulfonic acid, Titanium dioxide, Trolamine Salicylate and zinc oxide.

Hair treatment materials, other than those covered in the previous ingredient list. This includes cationic conditioning agents comprising tertiary and quaternary amino groups (e.g., quaternium-70, quaternium-80, stearamidopropyl dimethylamine, behentrimonium methosulfate, dicocodimonium chloride, dicetyldimonium chloride, distearyldimonium chloride hydroxyethyl cetyldimonium phosphate). Further, UV and color protectants (e.g., dimethylpabamidopropyl laurdimonium tosylate), heat protectants and styling polymers (e.g., vinyl pyrrolidone and vinylcaprolactam derivatives, such as PVP vinyl Caprolactam/DMAPA Acrylates Copolymer).

Consumer and agrichemical ingredients include insecticides and insect repellants, including, N,N-Diethyl-meta-toluamide, IR3535, Icaridin, Picaridin, Saltidin, Citronella, Permethrin, Neem oil and Lemon Eucalyptus.

Core materials also include polymeric materials, especially oil-soluble polymeric materials, which have film-forming properties on skin and hair, such as VP/Hexadecene Copolymer, Tricontanyl PVP and VP/Eicosene Copolymer as well as cosmetic and personal care actives, which are used for the conditioning or cosmetic treatment of skin, hair or nails are listed extensively and typically covered in IP.com publications IPCOM000128968D published 23 Sep. 2005 and IPCOM000133874D published Feb. 13, 2006, the contents of which are hereby incorporated by reference.

Core materials also include corrosion inhibitors which may be selected from the group consisting of carboxylic acids and derivatives such as aliphatic fatty acid derivatives, imidazolines and derivatives; including amides, quaternary ammonium salts, rosin derivatives, amines, pyridine compounds, trithione compounds, heterocyclic sulfur compounds, quinoline compounds, or salts, quats, or polymers of any of these, and mixtures thereof. For example, suitable inhibitors include primary, secondary, and tertiary monoamines; diamines; amides; polyethoxylated amines, diamines or amides; salts of such materials; and amphoteric compounds. Still other examples include imidazolines having both straight and branched alkyl chains, phosphate esters, and sulfur containing compounds.

Similarly, core materials include lipophilic scale inhibitors including those based on phosphate esters, and polyacrylates as well as oxidizing agents including inorganic or organic peroxides such as calcium peroxide, magnesium peroxides and lauryl peroxides.

As noted above, it may be desirable, if not necessary, to employ processing aids to assist in the production of the microcapsules. Two areas where processing aids are especially beneficial is in the solubilization/dispersion of the peptide in the water phase and in the dispersion or emulsification of the oil phase in the water phase or, if applicable, the dispersion or emulsification of the water phase in the oil phase. Generally speaking, the use of such processing aids is most beneficial where the core material is difficult to mill, particularly where it is otherwise difficult to obtain the target or desired size during the emulsification process. Preferred processing aids are emulsifiers and surfactants.

Emulsifiers of all types are suitable for use in the practice of the present process though it is to be appreciated, and those skilled in the art will readily recognize that different systems, e.g., different peptides, oil phases and core materials, will be better suited with one or more classes of emulsifiers than others. Specifically, while the present teachings are applicable to anionic, cationic, non-ionic and amphoteric emulsifiers generally, preferred emulsifiers are the cationic and non-ionic emulsifiers, particularly those having polyalkylether units, especially polyethylene oxide units, with degrees of polymerization of the alkylene ether unit of greater than about 6. Preferred emulsifiers are those which significantly reduce the interfacial tension between the continuous water phase and dispersed oil phase composition, and thereby reduce the tendency for droplet coalescence. In this regard, generally the emulsifiers for use in the water phase for aiding in the oil in water emulsion or dispersion will have HLB values of from 11 to 17.

Exemplary emulsifiers include, but are not limited to polyvinyl alcohols, including PVA itself and especially those polyvinyl alcohols that are partially hydrolyzed; cellulose derivatives such as ethyl hydroxyethyl cellulose, 2-hydroxyethyl cellulose, hydroxybutyl methylcellulose, hydroxypropyl methylcellulose, etc.; gums such as acacia gum and xantham gum; poly(meth)acrylic acids and derivatives; and poly(styrene-co-maleic acid) and derivatives; and the like. Most preferably, the emulsifier/emulsion stabilizer is a polyvinyl alcohol, particularly a polyvinyl alcohol that has been derived from polyvinyl acetate, wherein between 85 and 95%, preferably 88 to 90% of the vinyl acetate groups have been hydrolyzed to vinyl alcohol units.

Additional exemplary anionic surfactants and classes of anionic surfactants suitable for use in the practice of the present invention include: sulfonates; sulfates; sulfosuccinates; sarcosinates; alcohol sulfates; alcohol ether sulfates; alkylaryl ether sulfates; alkylaryl sulfonates such as alkylbenzene sulfonates and alkylnaphthalene sulfonates and salts thereof; alkyl sulfonates; mono- or di-phosphate esters of polyalkoxylated alkyl alcohols or alkylphenols; mono- or di-sulfosuccinate esters of $C_{12}$ to $C_{15}$ alkanols or polyalkoxylated $C_{12}$ to $C_{15}$ alkanols; ether carboxylates, especially alcohol ether carboxylates; phenolic ether carboxylates; polybasic acid esters of ethoxylated polyoxyalkylene glycols consisting of oxybutylene or the residue of tetrahydrofuran; sulfoalkylamides and salts thereof such as N-methyl-N-oleoyltaurate Na salt; polyoxyalkylene alkylphenol carboxylates; polyoxyalkylene alcohol carboxylates alkyl polyglycoside/alkenyl succinic anhydride condensation products; alkyl ester sulfates; naphthalene sulfonates; naphthalene formaldehyde condensates; alkyl sulfonamides; sulfonated aliphatic polyesters; sulfate esters of styrylphenyl alkoxylates; and sulfonate esters of styrylphenyl alkoxylates and their corresponding sodium, potassium, calcium, magnesium, zinc, ammonium, alkylammonium, diethanolammonium, or triethanolammonium salts; salts of ligninsulfonic acid such as the sodium, potassium, magnesium, calcium or ammonium salt; polyarylphenol polyalkoxyether sulfates and polyarylphenol polyalkoxyether phosphates; and sulfated alkyl phenol ethoxylates and phosphated alkyl phenol ethoxylates; sodium lauryl sulfate; sodium laureth sulfate; ammonium lauryl sulfate; ammonium laureth sulfate; sodium methyl cocoyl taurate; sodium lauroyl sarcosinate; sodium cocoyl sarcosinate; potassium coco hydrolyzed collagen; TEA (triethanolamine) lauryl sulfate; TEA (Triethanolamine) laureth sulfate; lauryl or cocoyl sarcosine; disodium oleamide sulfosuccinate; disodium laureth sulfosuccinate; disodium dioctyl sulfosuccinate; N-methyl-N-oleoyltaurate Na salt; tristyrylphenol sulphate; ethoxylated lignin sulfonate; ethoxylated nonylphenol phosphate ester; calcium alkylbenzene sulfonate; ethoxylated tridecylalcohol phosphate ester; dialkyl sulfosuccinates; perfluoro ($C_6$-$C_{18}$)alkyl phosphonic acids; perfluoro($C_6$-$C_{18}$)alkyl-phosphinic acids; perfluoro ($C_3$-$C_{20}$)alkyl esters of carboxylic acids; alkenyl succinic acid diglucamides; alkenyl succinic acid alkoxylates; sodium dialkyl sulfosuccinates; and alkenyl succinic acid alkylpolyglykosides. Further exemplification of suitable anionic emulsifiers include, but are not limited to, water-soluble salts of alkyl sulfates, alkyl ether sulfates, alkyl isothionates, alkyl carboxylates, alkyl sulfosuccinates, alkyl succinamates, alkyl sulfate salts such as sodium dodecyl sulfate (SDS), alkyl sarcosinates, alkyl derivatives of protein hydrolyzates, acyl aspartates, alkyl or alkyl ether or alkylaryl ether phosphate esters, sodium dodecyl sulphate, phospholipids or lecithin, or soaps, sodium, potassium or ammonium stearate, oleate or palmitate, alkylarylsulfonic acid salts such as sodium dodecylbenzenesulfonate, sodium dialkylsulfosuccinates, dioctyl sulfosuccinate, sodium dilaurylsulfosuccinate, poly(styrene sulfonate) sodium salt, alkylene-maleic anhydride copolymers such as isobutylene-maleic anhydride copolymer, or ethylene maleic anhydride copolymer gum arabic, sodium alginate, carboxymethylcellulose, cellulose sulfate and pectin, poly(styrene sulfonate), pectic acid, tragacanth gum, almond gum and agar; semi-synthetic polymers such as carboxymethyl cellulose, sulfated cellulose, sulfated methylcellulose, carboxymethyl starch, phosphated starch, lignin sulfonic acid; maleic anhydride copolymers (including hydrolyzates thereof), polyacrylic acid, polymethacrylic acid, acrylic acid alkyl acrylate copolymers such as acrylic acid butyl acrylate copolymer or crotonic acid homopolymers and copolymers, vinylbenzenesulfonic acid or 2-acrylamido-2-methylpropanesulfonic acid homopolymers and copolymers, and partial amide or partial ester of such polymers and copolymers, carboxy-modified polyvinyl alcohol, sulfonic acid-modified polyvinyl alcohol and phosphoric acid-modified polyvinyl alcohol, phosphated or sulfated tristyrylphenol ethoxylates.

Exemplary amphoteric and cationic emulsifiers include alkylpolyglycosides; betaines; sulfobetaines; glycinates; alkanol amides of $C_8$ to $C_{18}$ fatty acids and $C_8$ to $C_{18}$ fatty amine polyalkoxylates; $C_{10}$ to $C_{18}$ alkyldimethylbenzylammonium chlorides; coconut alkyldimethylaminoacetic acids; phosphate esters of $C_8$ to $C_{18}$ fatty amine polyalkoxylates; alkylpolyglycosides (APG) obtainable from an acid-catalyzed Fischer reaction of starch or glucose syrups with fatty alcohols, in particular $C_8$ to $C_{18}$ alcohols, especially the $C_8$ to $C_{10}$ and $C_{12}$ to $C_{14}$ alkylpolyglycosides having a degree of polymerization of 1.3 to 1.6, in particular 1.4 or 1.5. Additional cationic emulsifiers include quaternary ammonium compounds with a long-chain aliphatic radical, e.g., distearyldiammonium chloride, and fatty amines. Among the cationic emulsifiers which may be mentioned are alkyldimethylbenzylammonium halides, alkyldimethylethyl ammonium halides, etc. specific cationic emulsifiers include palmitamidopropyl trimonium chloride, distearyl diimonium chloride, cetyltrimethylammonium chloride, and polyethyleneimine. Additional amphoteric emulsifiers include alkylaminoalkane carboxylic acids betaines, sulphobetaines, imidazoline derivatives, lauroamphoglycinate, sodium cocoaminopropionate, and the zwitterionic emulsifier cocoamidopropyl betaine.

Suitable non-ionic emulsifiers are characterized as having at least one non-ionic hydrophilic functional group. Preferred non-ionic hydrophilic functional groups are alcohols and amides and combinations thereof. Examples of non-ionic emulsifiers include: mono and diglycerides; polyarylphenol polyethoxy ethers; polyalkylphenol polyethoxy ethers; polyglycol ether derivatives of saturated fatty acids; polyglycol ether derivatives of unsaturated fatty acids; polyglycol ether derivatives of aliphatic alcohols; polyglycol ether derivatives of cycloaliphatic alcohols; fatty acid esters of polyoxyethylene sorbitan; alkoxylated vegetable oils; alkoxylated acetylenic diols; polyalkoxylated alkylphenols; fatty acid alkoxylates; sorbitan alkoxylates; sorbitol esters; $C_8$ to $C_{22}$ alkyl or alkenyl polyglycosides; polyalkoxy styrylaryl ethers; amine oxides especially alkylamine oxides; block copolymer ethers; polyalkoxylated fatty glyceride; polyalkylene glycol ethers; linear aliphatic or aromatic polyesters; organo silicones; polyaryl phenols; sorbitol ester alkoxylates; and mono- and diesters of ethylene glycol and mixtures thereof; ethoxylated tristyrylphenol; ethoxylated fatty alcohol; ethoxylated lauryl alcohol; ethoxylated castor oil; and ethoxylated nonylphenol; alkoxylated alcohols, amines or acids; amides of fatty acids such as stearamide, lauramide diethanolamide, and lauramide monoethanolamide; long chain fatty alcohols such as cetyl alcohol and stearyl alcohol; glycerol esters such as glyceryl laurate; polyoxyalkylene glycols and alkyl and aryl ethers of polyoxyalkylene glycols such as polyoxyethylene glycol nonylphenyl ether and polypropylene glycol stearyl ether. Polyethylene glycol oligomers and alkyl or aryl ethers or esters of oligomeric polyethylene glycol are preferred. Also preferred as non-ionic emulsifiers are polyvinyl alcohol, polyvinyl acetate, copolymers of polyvinyl alcohol and polyvinylacetate, carboxylated or partially hydrolyzed polyvinyl alcohol, methyl cellulose, various latex materials, stearates, lecithins, and various surfactants. It is known that polyvinyl alcohol is typically prepared by the partial or complete hydrolysis of polyvinyl acetate. Accordingly, by reference to polyvinyl alcohol we intend to include both completely and partially hydrolyzed polyvinyl acetate. With respect to the latter, it is preferred that the polyvinyl acetate be at least 50 mole % hydrolyzed, more preferably, at least 75 mole % hydrolyzed.

Where the emulsifier is a polymeric emulsifier, especially one having or derived from an acrylic ester, e.g., a polyacrylate, the molecular weight is generally at least 10,000, preferably at least 20,000, most preferably 30,000 or more. Additionally, the amount of emulsifier is typically from about 0.1 to about 40% by weight, more preferably from about 0.2 to about 15 percent, most preferably from about 0.5 to about 10 percent by weight based on the total weight of the formulation. It is to be appreciated that certain acrylic polymers and copolymers may perform both as an emulsifier as well as a polymerizable and/or non-polymerizable component in forming the microcapsule wall. With respect to the latter, the polymeric emulsifier, particularly those in the nature of higher molecular weight polymers, are trapped and/or incorporated into the polymer wall as it is formed. This is especially likely where the nature of the water phase changes and the solubilized polymer comes out of solution.

Though not required, it may be desirable to employ other stabilizing substances that may be used, alone or in combination with the aforementioned materials, including ionic monomers. Typical cationic monomers include dialkyl amino alkyl acrylate or methacrylate including quaternary ammonium or acid addition salts and dialkyl amino alkyl acrylamide or methacrylamide including quaternary ammonium or acid addition salts. Typical anionic monomers include ethylenically unsaturated carboxylic or sulphonic monomers such as acrylic acid, methacrylic acid, itaconic acid, allyl sulphonic acid, vinyl sulphonic acid especially alkali metal or ammonium salts. Particularly preferred anionic monomers are ethylenically unsaturated sulphonic acids and salts thereof, especially 2-acrylamido-2-methyl propane sulphonic acid, and salts thereof.

Similarly, though not necessary, the water phase compositions and the core phase compositions may further contain other ingredients conventional in the art including, e.g., chain transfer agents and/or agents which help control the molecular weight/degree of polymerization of the wall forming monomer, thereby aiding in the movement of the oligomer/prepolymer through the respective oil phase and water phase compositions. Suitable chain transfer agents include, but are not limited to, lower alkyl alcohols having from 1 to 5 carbon atoms, mercaptoethanol, mercaptopropanol, thioglycolic acid, isooctylmercaptoproprionate, tert-nonylmercaptan, pentaerythritol tetrakis(3-mercaptopropionate), dodecylmercaptan, formic acid, halogenated hydrocarbons, such as bromoethane, bromotrichloromethane, or carbon tetrachloride, and the sulfate, bisulfate, hydrosulfate, phosphate, monohydrogen phosphate, dihydrogen phosphate, toluene sulfonate, and benzoate salts of sodium and potassium, especially sodium hypophosphite and sodium bisulfate. If present, the chain transfer agents are preferably used in amounts ranging from 0.01 to 5%, preferably from 0.5 to 3%, by weight with respect to the wall forming monomers and/or oligomers employed.

Following on the foregoing, the wall forming composition may also include various polyfunctional amines and alcohols which can be dispersed or dissolved in water or an aqueous solution and are capable of reacting with the isocyanate and/or chloroformate, especially the isocyanate, to serve as cross-linkers for modifying the microcapsule wall physical properties. In particular, the preferred cross-linkers can be employed to manipulate or control release characteristics while having minimal or modest impact upon degradability. Such cross-linking agents are well known in the art and generally have two or more, preferably two to five, primary or secondary amine groups or hydroxy groups or a combination of hydroxy and amine groups. Generally, they may be individual compounds, dimers, oligomers or low molecular weight polymers. Most especially, they tend to be lower molecular weight, generally having molecular weights of 500 or less, preferably 250 or less. Exemplary amines include 1,2-ethylenediamine, 1,3-diamino propane, 1,4-diaminobutane, 1,6-diaminohexane, hydrazine, 1,4-diaminocyclohexane, 1,3-diamino-1-methylpropane, diethylenetriamine, triethylenetetramine, tetraethylene-pentamine, bis(2-methylamino-ethyl) methylamine, triethanolamine, bis(dimethylamino-ethyl) ether, tri isopropanolamine, ethanolamine, guanidine amine and its derivatives, etc. Exemplary polyols include ethylene glycol, propylene glycol, diethylene glycol, dipropylene glycol, triethylene glycol, 2-ethylhexanediol-1,3 glycerin, 1,2,6-hexane triol, trimethylol propane, trimethylol ethane, and tris(hydroxy-phenyl) propane. If present, these cross-linking agents are preferably used in amounts ranging from 0.01 to 20%, preferably from 0.5 to 10%, by weight with respect to the wall forming monomers and/or oligomers employed. These cross-linkers may be added to the water phase prior to formation of the emulsion or to the emulsion once formed.

The particle size of the microcapsules of the present teaching will vary widely depending upon the core material as well as the intended end-use application, and the constraints of the method by which the microcapsules, especially the core material dispersion/emulsion, is formed. Typically, the volume weighted median particle size will range from about 2 microns to about 200 microns, preferably from about 5 microns to about 50 microns, most preferably from about 10 microns to about 20 microns. Volume Systems of Santa Barbara, CA.

In following, the thickness of the microcapsule walls is likewise dependent upon the intended end-use of the microcapsules and is influenced, as well, by the wall forming materials themselves and the physical properties of/desired of the microcapsule walls. Wall thickness is generally controlled by the amount of wall forming materials employed in the encapsulation process as well as the size/quantity of the beads of the dispersed phase to be encapsulated. Generally speaking, the wall forming materials comprise from 3 to 30, preferably from 5 to 20, more preferably from 8 to 15, weight percent of the microcapsule forming materials, i.e., wall forming materials and core materials.

Microencapsulation of the core material with the peptide-urethane, peptide-urea and peptide-urethane-urea microcapsule wall forming materials may be attained through any of the known methods for microencapsulation. Suitable techniques include coacervation, interfacial polymerization, air suspension, centrifugal extrusion, spray drying, pan coating, in-situ polymerization, and by forming a dispersion of core material and shell material and applying a pressure shock wave to the dispersion as described in Redding Jr. (U.S. Pat. No. 5,271,881, incorporated herein by reference). The specific selection of the method and the materials depends upon the nature, including the physical state and/or chemistry, of the material to be encapsulated, e.g., whether the carrier material is in a liquid form or a solid, semi-solid or gel-like particulate form. Exemplary methods are set forth in the following paragraphs as well as in, for example, Schwantes (U.S. Pat. No. 6,592,990), Nagai et. al. (U.S. Pat. No. 4,708,924), Baker et. al. (U.S. Pat. No. 4,166,152), Wojciak (U.S. Pat. No. 4,093,556), Matsukawa et. al. (U.S. Pat. No. 3,965,033), Matsukawa (U.S. Pat. No. 3,660,304), Ozono (U.S. Pat. No. 4,588,639), Irgarashi et. al. (U.S. Pat. No. 4,610,927), Brown et. al. (U.S. Pat. No. 4,552,811), Scher (U.S. Pat. No. 4,285,720), Shioi et. al. (U.S. Pat. No. 4,601,863), Kiritani et. al. (U.S. Pat. No. 3,886,085), Jahns et. al. (U.S. Pat. Nos. 5,596,051 and 5,292,835), Matson (U.S. Pat. No. 3,516,941), Chao (U.S. Pat. No. 6,375,872), Foris et. al. (U.S. Pat. Nos. 4,001,140; 4,087,376; 4,089,802 and 4,100,103), Greene et. al. (U.S. Pat. Nos. 2,800,458 and 2,730,456), Clark (U.S. Pat. No. 6,531,156), Saeki et. al. (U.S. Pat. Nos. 4,251,386 and 4,356,109), Hoshi et. al. (U.S. Pat. No. 4,221,710), Hayford (U.S. Pat. No. 4,444,699), Hasler et. al. (U.S. Pat. No. 5,105,823), Stevens (U.S. Pat. No. 4,197,346), Riecke (U.S. Pat. No. 4,622,267), Greiner et. al. (U.S. Pat. No. 4,547,429), and Tice et. al. (U.S. Pat. No. 5,407,609), among others and as taught by Herbig in the chapter entitled "Encapsulation" in Kirk Othmer, Encyclopedia of Chemical Technology, V.13, Second Edition, pages 436-456 and by Huber et. al. in "Capsular Adhesives", TAPPI, Vol. 49, No. 5, pages 41A-44A, May 1966, all of which are incorporated herein by reference.

Generally speaking, the first step in the encapsulation process is the preparation of discrete particles, domains or beads of the core material. Where such materials are in solution or liquid form and the encapsulation is to be by way of, e.g., coacervation, interfacial polymerization, etc., the solution or liquid containing the core material is subjected to high shear mixing or agitation to create a suspension, emulsion or colloidal system of discrete domains of the core material of the requisite size. Where the core material is a heat sensitive material, e.g., a wax or wax-like material, the carrier, with the therein incorporated core material, is heated above its melt temperature and then subjected to a similar high shear mixing or agitation in a liquid medium, preferably one of the wall forming materials or the phase material, e.g., water or oil phase, to create discrete droplets of the core material and then cooled to allow the solid particles to form, before encapsulating. Where the core material is a solid or substantially solid material, it may be ground and sorted to the desired particle size before encapsulation. Such methods, as well as additional alternative methods for preparation of the particles or discrete domains for encapsulation are widely used in industry and well known to those skilled in the art.

Although not limited thereto, the microcapsules according to the present teaching are preferably prepared by interfacial polymerization. Here, the core material is solubilized, dispersed or emulsified in a liquid solution of one of the materials to be used as/containing one of the wall forming materials, preferably the oil phase comprising the isocyanate, or, in the case of a water-in-oil-in-water system, in a first water phase, preferably free of wall forming material, which water phase containing the core material is then dispersed or emulsified in the oil phase which, in turn, is dispersed or emulsified in a second water phase, which is ultimately the continuous phase for the interfacial polymerization and contains the other wall forming material, namely the peptide.

As noted above, the microcapsules made in accordance with the present teaching have a myriad of commercial and consumer applications across most all industries and in many commercial products.

In one embodiment, microcapsules described herein may be incorporated in personal care products and compositions including, but not limited to, cosmetics, drug delivery systems, hair care products, skin treatment products and oils, pharmaceuticals, pigment dispersions, preservative compositions, skin coloring products, skin restorative products, styling products for hair, sunscreen and suntan lotions, sprays, oils, creams and the like, water proof/resistance products, wear resistance products and additives, shower gels, shampoos, and thermal protecting/enhancing compositions. Dental personal care compositions include denture adhesives, toothpastes, mouth washes, chewing gums and the like.

The microcapsules may be used in numerous pharmaceutical applications and compositions including peroral and topical dosage forms, such as tablets, pellets, capsules, dermatological products (creams, gels, ointments, sprays, lotions, and foams), transdermal patches and the like.

The microcapsules may also be used in conjunction with a myriad of agrochemicals, especially those listed extensively in U.S. Pat. No. 5,389,688, to ISP, which is incorporated herein by reference in its entirety.

In common consumer products, the microcapsules may be used to incorporate actives such as fabric conditioners, liquid laundering detergents, powdered laundering detergents, dish washing detergents, hard surface cleaners, anti-static agents, anti-odor agents, antimicrobial agents, etc., into various household cleaners and other "cleaning" products such as air fresheners, sprays, and the like, as well as onto textiles, paper and the like as surface modifiers or coatings.

The microcapsules of the invention can be advantageously used in controlling perfume release in fragrant consumer products. With the microcapsules of the present teaching there is a considerable improvement in longevity and intensity of the encapsulated perfume in actual use. Examples of consumer products comprising perfume microcapsules according to certain aspects of the present application may fall into product group categories of laundering detergents, cosmetics, personal care products, dish washing detergents and house cleaners. More specific examples of consumer products include fabric conditioners, liquid/powdered laundering detergents, dish washing detergents, hair shampoos, hair conditioners, hair styling gels, soaps, body washes, shower gels, all-purpose cleaners including hard surface cleaners, carpet cleaners, body lotions, antiperspirant/deodorants and spray-able products.

In following, in another embodiment of the present teaching there is provided a method for producing fragrance loaded microcapsules with improved substantivity for incorporation into, (i) laundry detergents; (ii) fabric softener compositions; and (iii) drier-added fabric softener articles, these when deposited on fabrics during laundry treatment and capable of remaining on the textile following initial application and which is capable of later being sheared by the application of mechanical force. Accordingly, the encapsulated fragrance provides a "burst" of fragrance during wear and/or cleaning due to breakage of the capsule wall.

Alternatively, the fragrance microcapsules of the present application can be formulated into solid fabric care compositions with polysaccharides such as sugars according to the procedure described in US patent No 2011/0082066, the contents of which are hereby incorporated by reference. The solid fabric care products can be used for delivering fragrances onto the textile articles during the washing/cleaning cycle and subsequently the laundered textiles have beneficial fragrance odor profile during the wear.

Alternatively, the fragrance microcapsules can be incorporated in 2-in-1 powdered detergent and conditioner compositions according to the processes described in U.S. Pat. Nos. 4,698,167 and 5,540,850 and also crystalline laundry additives as described in the US application 2011/97369 and PCT WO 2010/000558, which are incorporated herein by reference.

For some embodiments, it may be preferred to incorporate a plurality of core materials into a single microcapsule and/or provide mixtures of such microcapsules, For example, one may add one or more preservatives and/or antimicrobial agents in the delivery matrix in addition to the respective actives, such as, but not limited to, benzoic acid, sorbic acid, dehydroacetic acid, piroctone olamine, DMDM hydantoin, IPBC, triclosan, bronopol, isothiazolinones, parabens, phenoxyethanol, and combination thereof.

In another embodiment, the core material may be a phase change material or mixtures thereof for temperature control. Typical phase change materials exhibit a melting temperature from −20° C. to 100° C. and generally comprise linear or branched hydrocarbons or fatty esters or mixtures thereof, of different chain lengths and melting points. The microcapsules containing the phase change material core material can be coated or sprayed onto or incorporated into suitable materials including textile fibers, such as cotton and polyester, during the spinning process or coated directly onto textiles or incorporated into building construction material for example bricks, gypsum, and the like, to allow for temperature control by use of latent heat of fusion.

It is further contemplated that microcapsules of the present teaching can be used in the construction industry in conjunction with cements, plaster boards, breeze blocks, chipboards, heat transfer fluids, sealants, adhesives etc. In this instance, the core material can be a phase change material, biocide, flame retardant, catalyst, epoxy resin, etc.

The present microcapsules also have a number of automotive applications including the use of encapsulated phase change materials in the coolant systems, the use of encapsulated lubricant additives such as anti-wear additives in engine oils, and the use of encapsulated UV absorbers and/or anti-corrosive agents for car coatings.

The microcapsules described herein may also be used in conjunction with additives used in plastics such as flame retardants, catalysts, pigments, light stabilizers, UV absorbers, and the like, all of which can be encapsulated to allow higher compatibilities, longevity and self-healing of the plastic material. For example, the core material can be a catalyst for self-healing, an UV absorber for protection from photodamage due to UV light, or a thermochromic material for color change in coatings across a broad spectrum of industry.

The microcapsules according to the present teaching may also be used in oilfield applications. Here the microcapsules may contain traditional oilfield chemicals such as corrosion inhibitors, scale inhibitors, oxidizing agents, crosslinking agents, catalysts, acidizing agents, biocides, demulsifiers, enzymes, polymers, lubricants, shale inhibitors, solvents, and surfactants. The encapsulated oil field chemicals can be applied advantageously at the different petroleum extraction stages from drilling, cementing, stimulation to production and enhanced oil recovery. The release mechanisms of delivery of the oilfield chemical can be by temperature, dilution, pH and shear at the relevant points of applications.

EXAMPLES

A number of microcapsules were formed in accordance with the present teaching as well as a number of comparative microcapsules using materials outside of the scope of the limitations set forth herein. In those instances where the polypeptides were readily dispersible/soluble in the aqueous phase, no emulsifier was used: in those instances where dispersion/solubility was less than desired, an emulsifier was added, particularly in the case of the comparative examples. Typically, the microcapsules were formed in accordance with the following steps using non-water soluble core materials:

An aqueous phase solution was prepared by dissolving the peptides, with or without an emulsifier, in deionized water in a reactor vessel at a predetermined temperature.

An oil phase solution was prepared by mixing the core material to be encapsulated with the isocyanate(s), or other oil-soluble reactive, in another reactor vessel at a predetermined temperature.

The oil phase solution was then dispersed in the water phase solution under high shear milling at a predetermined temperature using a milling blade to form an oil-in-water emulsion with the high shear milling continuing until the targeted emulsion droplet size was attained.

Once the targeted droplet size was attained, milling with the milling blade was paused and an agitator employed to maintain the emulsion.

Optionally, a cross-linker was then added to the emulsion and mixed to evenly disperse the same.

The temperature of the emulsion was then raised over a period of time to the desired reaction temperature and then maintained at that temperature until the reaction/microcapsule formation was complete. Depending upon the selection of core and wall forming materials, the temperature was raised to, e.g., 65° C., 75° C. or 85° C. over a period of 1 hour, 2 hours or 4 hours and the reaction allowed to continue for up to 6 hours, up to 8 hours, even 10 or 30 hours.

At the end of the reaction, the resulting microcapsule slurry was allowed to cool to ambient temperature in the reactor vessel, after which the microcapsules were recovered from the slurry.

Although the preparation and milling of the solutions and mixture is preferably done at room temperature, it is to be appreciated that somewhat elevated temperatures may be desirable to aid in quicker and easier formation of the solutions and/or the emulsion. Furthermore, one may vary the milling temperature and/or the rate of temperature ramp up during wall formation depending on the reactivity and quantity of the raw materials used. In this respect, it is to be appreciated that the capsule slurry may become gelled, or emulsion become coalesced during temperature ramp up and/or wall formation if too high of a milling temperature and/or to fast a rate of temperature ramp up are used. In this respect, milling at room temperature is preferred if the raw materials are very reactive. On the other hand, higher milling temperature is preferred if the raw materials are less reactive.

The resulting microcapsules were evaluated for a number of physical characteristics and properties to demonstrate the utility and applicability including, particle size determination, free active, leakage, release properties and degradability.

Median Volume Weighted Particle Size

The volume-weighted median particle size of the microcapsules is measured using an Accusizer 780A, made by Particle Sizing Systems, Santa Barbara Calif., or equivalent. The instrument is calibrated from 0 to 300 μm (micrometer or micron) using particle size standards (as available from Duke/Thermo-Fisher-Scientific Inc., Waltham, Mass., USA). Samples for particle size evaluation are prepared by diluting about 0.5 g of microcapsule slurry in about 10 g of de-ionized water. This dilution is further diluted using about 1 g of the initially diluted solution in about 20 g of water. Approximately 1 g of the most dilute sample is injected into the Accusizer and the testing initiated using the autodilution feature. The Accusizer should read more than 8,500 counts/second. If the counts are below 8,500 additional sample is added. The sample is autodiluted until below 9,200 counts/second was measured, then particle counting, and size analysis is initiated. After 2 minutes of testing, the Accusizer displays the median volume-weighted particle size. Particle sizes stated herein are on a volume weighted basis and are to be understood as median volume weighted particle size, ascertainable by the above procedure.

Percent Free Beneficial Agent after Microencapsulation

Characterization of free benefit agent in microcapsule suspension: 0.40-0.45 g of the microcapsule suspension is weighed and mixed with 10 ml of hexane. The sample is mixed by vortexing at 3000 rpm for 10 seconds to leach the free oil from the microcapsule suspension and then set aside for no more than one minute. An aliquot is removed from the hexane layer and filtered through a 0.45 μm syringe filter. The concentration of benefit agent in the hexane is measured using an Agilent 7800 Gas Chromatograph (GC), Column: ZB-1HT (10 meter×0.32 mm×0.25 μm), Temp: 50° C. for 1 minute then heat to 270° C. @ 10° C./min, Injector: 275° C., Detector: 325° C., 2 μl injection.

Degradability

Biodegradability of the microcapsules was determined in accordance with the OECD 301B test method. This test method classifies microcapsules as "Readily degradable" if the microcapsules show a degree of degradation of >60% in up to 28 days and as "Enhanced/modified readily biodegradable" if the degree of degradation is >60% in up to 60 days.

Release of Captex 355

The premise of this method is based on the CIPAC MT190. The capsule slurry is placed into a 110 ml jar. To this, a solution of hexane and ethanol (9:1) with an internal standard (dicyclohexyl phthalate) is added to the jar. The jar is placed on a horizontal roller, rolling at 70 RPM. At time intervals of 15, 30, 60, and 180 minutes, exactly 1 ml of solution is removed and placed into an injection vial. The injection vial is then analyzed via GC-FID for the core of interest.

Release of Fragrance Oil RA into Liquid Matrices

The microcapsules were evaluated for release properties, i.e., release of the fragrance, in a heavy-duty liquid laundry detergent (HDL) from Seventh Generation, Inc. and in a commercial liquid fabric enhancer (LFE—unscented Downy® fabric softener). A sample of LFE or HDL is weighed into a 50 ml glass jar. To this, a specified amount of capsule slurry is added and thoroughly mixed. After mixing, the jar is tightly capped and placed into an oven at 35° C. for one week. After the week has elapsed, the sample is removed from the oven. A sample aliquot is removed from the jar into a Scintillation vial. A small amount of water is added and gently mixed, ensuring no foam is generated. To this, hexane is added to extract the core for analysis via minor mixing. The solution is allowed to sit to separate and then the hexane layer is sampled to be analyzed via GC-FID.

Example 1

Microcapsules according to the present teaching were prepared by forming a water phase solution by dissolving 10 grams of PEPTIPLUS® XP polypeptide with molecular weight of 2,500 to 4,000 Dalton (Da) from GELITA USA, Inc. in 160 grams of deionized water in a beaker at ambient temperature. The capsule core composition was prepared in a reactor at ambient temperature by mixing 60 grams of a fragrance blend comprising a combination of common odiferous compounds including benzyl acetate, isobornyl acetate, hexyl salicylate, and the like, with 60 grams of Captex® 355 caprylic/capric triglyceride from ABITEC Corporation (fragrance diluent). 5 grams of Mondur® MR aromatic isocyanate from Covestro LLC was then added to the reactor under agitation by a mixer blade. The agitation mixer blade was paused and replaced with a milling blade. The water phase was then added to the reactor gradually under high shear milling: the high shear milling maintained until the targeted emulsion droplet size of around 10 microns was attained.

Once the target emulsion droplet size was achieved, milling was paused, and the milling blade switched out for the mixer blade to keep the emulsion mixed. Thereafter, the temperature of the reactor vessel was raised from ambient to 50° C. over a period of 60 min, and the temperature maintained at 50° C. for an additional 60 min. Subsequently, temperature was then raised to 65° C. over 60 min, and maintained at 65° C. for an additional 120 min. Thereafter, the temperature was raised to 85° C. over a period of 60 min, and maintained at 85° C. for an additional four hours, at which time the process was deemed complete. The resulting microcapsule slurry in the reactor was allowed to cool to ambient temperature. The slurry was found to be of low viscosity and generally uniform and smooth with no visible thickening and/or agglomeration. A photomicrograph of the microcapsule is presented in FIG. 1.

Example 2

A microcapsule slurry was prepared in accordance with the process of Example 1 except that the amount of PEPTIPLUS® XP polypeptide was reduced to 10 grams.

Example 3

A microcapsule slurry was prepared in accordance with the process of Example 1 except that 0.2 grams of diethylenetriamine (DETA) was added into the emulsion after milling and prior to temperature ramp up.

Example 4

A microcapsule slurry was prepared in accordance with the process of Example 1 except that 2.7 grams of DETA was added into the emulsion after milling and prior to temperature ramp up.

Example 5

A microcapsule slurry was prepared in accordance with the process of Example 1 except that PEPTIPLUS® XP polypeptide was replaced with Verisol® B polypeptide (1700-2300 Da) from GELITA USA, Inc.

Example 6

A microcapsule slurry was prepared in accordance with the process of Example 1 except that PEPTIPLUS® XP polypeptide was replaced with Fortibone® polypeptide (4700-5300 Da) from GELITA USA, Inc.

Example 7 (Comparative Example)

A comparative microcapsule slurry was prepared in accordance with the process of Example 1. Here, a first water phase (WP1) solution was prepared by mixing 2.7 grams of Stepanol® WA EXTRA K sodium lauryl sulfate anionic surfactant in 250 grams of deionized water in a beaker at ambient temperature. A second water phase (WP2) was prepared by dissolving 10 grams of pork gelatin (50,000-70,000 Da) from GELITA USA, Inc. in 45 grams of deionized water at 50° C. for 30 min. The capsule core composition was prepared by mixing 89 grams of the aforementioned fragrance blend with 89 grams of Captex® 355 caprylic/capric triglyceride in a reactor using a mixing blade. Thereafter 15 grams of Mondur® MR aromatic isocyanate was added with mixing. The mixer was paused and WP1 was added into the reactor and the mixer blade replaced with a milling blade. The mixture was milled until the targeted emulsion droplet size of around 10 microns was achieved. The milling was paused, and the milling blade replaced by the mixing blade and mixing resumed in order to keep the emulsion mixed as WP2 was slowly added to the reactor. Thereafter, the reaction was allowed to proceed as in Example 1. The resulting slurry of gelatin microcapsules was found to thicken at temperature below 35° C. and became gelled at room temperature.

Example 8 (Comparative Example)

A second comparative microcapsule slurry was prepared in accordance with the process of Example 7 except that 1.6 grams of DETA was added into the emulsion after milling and prior to temperature ramp up.

Example 9 (Comparative Example)

A third comparative microcapsule slurry was prepared by forming a water phase solution by mixing 2.2 grams of Stepanol® WA EXTRA K sodium lauryl sulfate anionic surfactant in 206.6 grams of deionized water in a beaker at ambient temperature. The capsule core composition was prepared in a reactor at ambient temperature by mixing 70.5 grams of the fragrance blend with 70.5 grams of Captex® 355 caprylic/capric triglyceride. 9.5 grams of Mondur® MR aromatic isocyanate was then added to the reactor under agitation by a mixer blade. Once the addition was completed, the agitation mixer blade was paused and replaced with a milling blade. The water phase was added to the reactor, and then high shear milling was started. The high shear milling maintained until the targeted emulsion droplet size of around 10 microns was attained.

Once the target emulsion droplet size was achieved, milling was paused, and the milling blade was switched out for the mixer blade to keep the emulsion mixed. Then 39.7 grams of 20% L-lysine monohydrochloride solution (Sigma-Aldrich) was slowly added into the reactor. pH was adjusted to 9.0 by addition of sodium hydroxide solution. Thereafter, the reaction was allowed to proceed as in Example 1. The slurry was found to be of low viscosity and generally uniform and smooth with no visible thickening and/or agglomeration.

Example 10 (Comparative Example)

A fourth comparative microcapsule slurry was prepared by forming a water phase solution by mixing 2.6 grams of Stepanol® WA EXTRA K sodium lauryl sulfate anionic surfactant in 189.1 grams of deionized water in a beaker at ambient temperature. The capsule core composition was prepared in a reactor at ambient temperature by mixing 83.9 grams of the fragrance blend with 83.9 grams of Captex® 355 caprylic/capric triglyceride. 11.4 grams of Mondur® MR aromatic isocyanate was then added to the reactor under agitation by a mixer blade. The agitation mixer blade was paused and replaced with a milling blade. The water phase was then added to the reactor gradually with high shear milling: the high shear milling maintained until the targeted emulsion droplet size of around 10 microns was attained.

Once the target emulsion droplet size was achieved, milling was paused, and the milling blade was switched out for the mixer blade to keep the emulsion mixed. Then 23.6 grams of 20% L-lysine monohydrochloride solution was slowly added into the reactor. The pH of the mixture was adjusted to 9.0 by addition of sodium hydroxide solution. Thereafter, the reaction was allowed to proceed as in Example 1. The resulting slurry was found to be of low viscosity and generally uniform and smooth with no visible thickening and/or agglomeration.

Example 11 (Comparative Example)

A fifth comparative microcapsule slurry was prepared by forming a water phase solution by mixing 95.26 grams of 5% Selvol® 540 polyvinyl alcohol solution in 122.27 grams of deionized water in a beaker at ambient temperature. The capsule core composition was prepared in a reactor at ambient temperature by mixing 73.49 grams of the fragrance blend with 73.49 grams of Captex® 355 caprylic/capric triglyceride. 9.94 grams of Mondur® MR aromatic isocyanate was then added to the reactor under agitation by a mixer blade. The agitation mixer blade was paused and replaced with a milling blade. The water phase was added to the reactor, and then high shear milling was started. The high shear milling was maintained until the targeted emulsion droplet size of around 10 microns was attained.

Once the target emulsion droplet size was achieved, milling was paused, and the milling blade was switched out for the mixer blade to keep the emulsion mixed. Then 20.71 grams of 20% L-Arginine monohydrochloride solution (Sigma Aldrich) was slowly added into the reactor. The pH was adjusted to 9.0 by addition of sodium hydroxide solution. Thereafter, the reaction was allowed to proceed as in Example 1. The slurry was found to be of low viscosity and generally uniform and smooth with no visible thickening and/or agglomeration.

Example 12 (Comparative Example)

A sixth comparative microcapsule slurry was prepared in accordance with the process of Example 11 except that L-Arginine monohydrochloride was replaced by DETA (Akzo Nobel Functional Chemicals K64658).

Example 13-16

A series of microcapsule slurries were prepared in accordance with the process of Example 1 except that PEPTIPLUS® XP polypeptide was replaced with PEPTIPLUS® SP polypeptide (2500-4000 Da) in each of the examples, and the pH of the emulsion was adjusted to 4, 5, 7 and 9, respectively, prior to temperature ramp up.

Example 17

A microcapsule slurry was prepared in accordance with the process of Example 1 except that 0.5 grams of Jeffcat® ZF-20 bis(dimethylaminoethyl)ether (Huntsman Corp.) was added into the emulsion after milling and prior to temperature ramp up.

Example 18-21

A further series of microcapsule slurries was prepared in accordance with the process of Example 1 except that Mondur® MR aromatic isocyanate was replaced with Desmodur® N3300A, Takenate® D-110N, Desmodur® N3400, and Desmodur® N3200A, respectively, each an aliphatic polyisocyanate (the Desmodur® variants based on HDI trimer from Covestro LLC and the Takenate® based on hydrogenated XDI from Mitsui Chemicals, Inc.).

Microcapsule Property Comparison

Table 1 presents an overview of the formulation of each of the foregoing microcapsules as well as the property profiles thereof. The two critical characteristics evaluated pertain to the wall integrity, specifically the ability of the microcapsules to release their contents without having to fracture the microcapsule walls, and degradability, the latter a measure of the microcapsules ability to degrade once released into the environment. As noted above, these microcapsules have a myriad of applications across multiple industries and consumer applications. One particular application, and that which these examples are directed to, is in laundry care where it is desirable to impart a fragrance to clothes being cleaned. Accordingly, the release characteristics were evaluated on two fronts. The first was to evaluate the release rate of the carrier material, the Captex triglyceride as its release speaks to the longevity of the microcapsules, essentially, if too much carrier is released, the microcapsules essentially dry out. The second was to evaluate the release characteristics of the fragrance blend: in this instance, in the presence of a heavy-duty laundry detergent (HDL—from Seventh Generation Inc.) and in the presence of a liquid fabric enhancer (LFE—Downy® fabric softener from P&G). Release characteristics are essential to the useful life of the product and the efficacy of the product for its intended purpose. The second critical characteristic is degradability, this is particularly so given the ever-growing concern and debate over the use and release into the environment of microplastics. Indeed, regulatory restrictions and controls are already in place in certain countries and regions and more are in process. Hence, the objective as sought and achieved by the microcapsules of the present teaching is controlled release and degradability: a combination of properties not attained by existing microcapsules.

Figure 2:
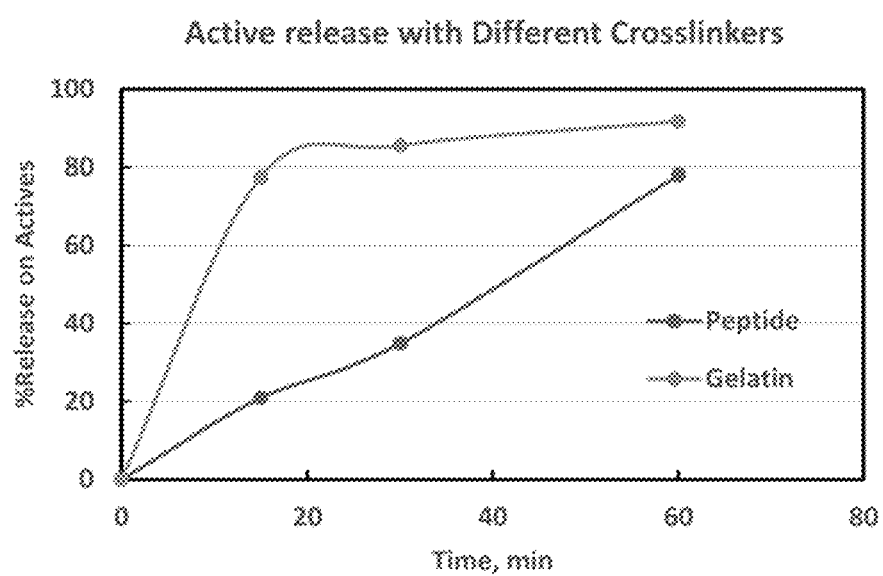
FIG. 2 is a graph of the release profile of two microcapsules, one according to the present teaching and one where gelatin is used instead of the peptide.

Turning to Table 1, as indicated under the heading Wall %, the microcapsules according to the present teaching and the comparative microcapsules all had fairly similar wall to core ratios. This is indicative of a similar load of the therein contained fragrance blend composition, enabling a proper comparison of release performance. As evident from the results in Table 1, the release characteristics of the microcapsules varied markedly depending upon the selection of the co-reactant for the isocyanate and the presence of an additional cross-linker. For the most part, the examples according to the present teaching, Examples 1-6 and 13-17, employing the polypeptides as the co-reactant, demonstrated controlled, longer term release of the fragrance carrier, the Captex 355, as compared to the gelatin-based co-reactant, Example 7, indicative of a longer lived product and equivalent, if not modestly better, or even marked improvement in fragrance release: depending upon the selection of wall-forming reactants and their weight ratio. FIG. 2 presents the release characteristics of the microcapsules of Example 1 as compared to the microcapsules of the comparative example, Example 7. Clearly a marked difference in release is demonstrated with those according to the present teaching having a steady, slow release whereas the comparative microcapsule had a massive, quick release, leaving little for long-term effect.

Table 1 also shows that the addition of relatively minor amounts of an additional cross-linker, specifically, DETA, slowed the release properties overall with both the polypeptide and gelatin co-reactant microcapsules, Examples 3-4 and Example 8, respectively; however, as noted below, the presence of the co-reactant in the comparative microcapsules of Example 8 did not address the lack of degradability. While the comparative microcapsules using individual amino acids as the co-reactants, Examples 9-11, had relatively good release capabilities, like the gelatin-based microcapsules, as will be discussed below, these too failed with respect to their degradability. Furthermore, unlike the use of the claimed polypeptides with the aromatic isocyanate, both sets of comparative examples, specifically those using gelatin and those using amino acids as the co-reactant, required the additional presence of an emulsifier to form good/sufficient dispersions in the micro-encapsulation processes. On the other hand, irrespective of the co-reactant, the use of an emulsifier was found preferred, if not necessary, even with the polypeptides where the isocyanate was an aliphatic isocyanate: though it is unclear whether this is applicable to all aliphatic isocyanates or just those of the molecular weight range of those employed (See, Examples, 18-21). Still, these microcapsules demonstrated good release characteristics.

As noted above, perhaps the most critical aspect of the microcapsules of the present teaching is their degradability, particularly degradability without compromising the release characteristics. As shown in Table 1, all of the microcapsules according to the present teaching achieved marked improved degradability as compared to the comparative microcapsules using individual amino acids or gelatin. Indeed, the microcapsules of Examples 1 and 5 achieved the "holy grail" of degradability designations, "Readily Degradable", under the guidelines of the Organisation for Economic Co-operation and Development (OECD). The remaining examples all came close and demonstrated marked degradability as compared to the microcapsules of the comparative examples.

Example 22

A further microcapsule slurry demonstrating the embodiment wherein the isocyanate is replaced with a bischloroformate is prepared by adding 40.68 grams of 5% Selvol® 540 polyvinyl alcohol solution to a solution comprising 13.56 grams of Peptiplus® SP polypeptide dissolved in 176.27 grams of deionized water in a beaker at ambient temperature. A capsule core composition is prepared comprising the mixture of 81.36 grams of the fragrance blend and 81.36 grams of Captex® 355 caprylic/capric triglyceride. 10 grams of triethyleneglycol bischloroformate from Sigma Aldrich is then added to the reactor under agitation by a mixer blade. At that point, the agitation mixer blade is paused and replaced with a milling blade. The water phase is then added to the reactor under high shear milling which is continued until the targeted emulsion droplet size of around 10 microns is attained.

Once the target emulsion droplet size is achieved, milling is paused, and the milling blade switched out for a mixer blade to keep the emulsion mixed. As necessary or desirable, a 20% caustic solution is used to adjust pH of the slurry. Thereafter, temperature of the reactor is raised to 65° C. in 60 min, and maintained at 65° C. for 2 hours.

Example 23

A microcapsule slurry is prepared in accordance with the process of Example 22 except that 0.5 grams of DETA is added into the emulsion after milling and prior to temperature ramp up.

TABLE 1

| Example | Oil Phase Isocyanates | weight, g | Water Phase Reactants | weight, g | Wall % | Emulsifier | Captex 355 % Release min | | | Fragrance Dead % Release 35° C., One Week | | | % Degradation Days | | | | | | |
|---|---|---|---|---|---|---|---|---|---|---|---|---|---|---|---|---|---|---|---|
| | | | | | | | 15 | 30 | 60 | HDL | LF | 8 | 15 | 22 | 28 | 4 | 50 | 57 | 62 |
| 1 | Mondur MR | 5 | Peptiplux XP | 10 | 11.11 | n/a | 20.90 | 34.87 | 78.00 | 41.04 | 25.88 | 38.41 | 54.73 | 60.77 | 63.16 | 70.02 | 79.27 | 85.26 | 91.98 |
| 2 | Mondur MR | 5 | Peptiplus XP | 5 | 7.96 | n/a | 12.44 | 24.95 | 46.37 | 60.89 | 40.84 | 23.32 | 25.49 | 25.81 | 26.37 | 46.01 | 46.53 | 46.91 | 47.17 |
| 3 | Mondur MR | 5 | Peptiplus XP, 0.2 g DETA | 10 | 11.18 | n/a | 9.13 | 21.23 | 41.43 | 22.79 | 16.04 | 36.85 | 42.79 | 44.36 | 45.18 | 45.56 | 48.77 | 50.88 | 53.43 |
| 4 | Mondur MR | 5 | Peptiplus XP, 2.7 g DETA | 10 | 12.41 | n/a | 6.40 | 10.23 | 20.71 | 16.94 | 9.49 | 21.76 | 29.35 | 34.58 | 37.91 | | | | |
| 5 | Mondur MR | 5 | Verisol 8 | 10 | 11.11 | n/a | 11.51 | 21.56 | 39.01 | 55.84 | 30.66 | 67.03 | 76.54 | 78.79 | 79.63 | | | | |
| 6 | Mondur MR | 5 | Fortibone | 10 | 11.11 | n/a | 21.12 | 36.87 | 60.71 | 65.77 | 36.52 | 32.95 | 36.62 | 38.06 | 39.91 | | | | |
| 7 | Mondur MR | 1 | gelatin | 11 | 10.58 | WA Extra K | 84.64 | 90.11 | 94.08 | 35.5 | 35.54 | 7.96 | 11.61 | 13.72 | 15.05 | pulled | | | |
| 8 | Mondur MR | 10 | gelatin, 1.6 g DETA | 11 | 11.3 | WA Extra K | 16.19 | 34.23 | 59.48 | 34.49 | 25.37 | 8.45 | 11.21 | 11.87 | 12.23 | pulled | | | |
| 9 | Mondur MR | 9 | 20% LYS HCl | 39.72 | 11.79 | WA Extra K | 13.81 | 24.73 | 42.39 | 23.76 | 26.16 | 4.28 | 4.17 | 4.20 | 4.50 | | | | |
| 1 | Mondur MR | 1 | 20% LYS HCl | 23.64 | 9.55 | WA Extra K | 17.08 | 29.71 | 48.19 | 31.95 | 27.80 | 2.10 | 1.83 | 1.86 | 1.88 | | | | |
| 1 | Mondur MR | 9 | 20% ARG HCl | 20.71 | 11.79 | Selvol S40 | 18.62 | 37.34 | 64.01 | 40.08 | 31.52 | 4.22 | 4.19 | 6.28 | 8.20 | | | | |
| 1 | Mondur MR | 10.54 | K64658, 1.4 g | 1.4 | 10.77 | Selvol S40 | 11.71 | 24.76 | 44.21 | 23.47 | 20.83 | 8.58 | 10.86 | 12.75 | 14.83 | | | | |
| 1 | Mondur MR | 5 | Peptiplus SP, pH4 | 10 | 11.11 | n/a | 17.35 | 32.57 | 59.22 | 67.50 | 37.76 | | | | | | | | |
| 1 | Mondur MR | 5 | Peptiplus SP, pH5 | 10 | 11.11 | n/a | 15.46 | 29.15 | 53.99 | 63.87 | 37.54 | | | | | | | | |
| 1 | Mondur MR | 5 | Peptiplus SP, pH7 | 10 | 11.11 | n/a | 15.21 | 31.64 | 59.34 | 51.03 | 33.35 | | | | | | | | |
| 1 | Mondur MR | 5 | Peptiplus SP, pH9 | 10 | 11.11 | n/a | 18.50 | 38.56 | 66.93 | 34.12 | 25.37 | | | | | | | | |
| 17 | Mondur MR | 5 | Peptiplus SP, pH5 with Jeffcat 0.5 g ZF-20 | 10 | 11.12 | n/a | 9.09 | 20.57 | 41.77 | 21.73 | 23.89 | | | | | | | | |
| 18 | Desmodur N3300A | 5 | Peptiplus SP, pH4 | 10 | 22.22 | Selvot S40 | 24.2 | 37.87 | 56.46 | 71.77 | 39.06 | | | | | | | | |
| 19 | Takenate D-110N | 5 | Peptiplus SP, pH5 | 10 | 11.11 | Selvol S40 | | | | 30.21 | 22.58 | | | | | | | | |
| 20 | Desmodur N3400 | 5 | Peptiplus SP, pH7 | 10 | 11.11 | Selvol S40 | 30.67 | 43.91 | 62.10 | 84.98 | 46.11 | | | | | | | | |
| 21 | Desmodur N3200A | 5 | Peptiplus SP, pH9 | 10 | 11.11 | Selvol S40 | 23.18 | 36.10 | 57.04 | 68.20 | 39.00 | | | | | | | | |

Example 24

A microcapsule slurry is prepared in accordance with the process of Example 1 except that 5 grams of diethylene glycol bischloroformate is added into the capsule core composition before milling.

Examples 24-33

A series of microcapsule slurries were prepared to demonstrate the different properties in forming microcapsules from a wholly aliphatic isocyanate—Example 24 and 33 (Takenate D110N and Desmodur N3200A, respectively), a wholly aromatic isocyanate—Example 27 (Mondur MR), a wholly cycloaliphatic isocyanate—Example 30 (Desmodur W), combinations of aliphatic and aromatic isocyanates—Examples 25 and 26 (Takenate D110N and Mondur MR), combinations of aliphatic isocyanates—Examples 31 and 32 (Takenate D110N and Desmodur N3200A) and combinations of aliphatic and cycloaliphatic isocyanates—Examples 28 and 29 (Takenate D110N and Desmodur W). The specific isocyanates employed and their amounts for each of the microcapsule forming compositions were as presented in Table 2. Generally speaking, the microcapsules were formed by preparing a water phase solution by dissolving 10 parts of PEPTIPLUS® SP polypeptide with molecular weight of 2,500 to 4,000 Dalton (Da) from GELITA USA, Inc. in 160 parts of deionized water in a beaker at ambient temperature. The capsule core composition was prepared in a reactor at ambient temperature by mixing 102 parts of a fragrance blend (RA) comprising a combination of common odiferous compounds including benzyl acetate, isobornyl acetate, hexyl salicylate, and the like, with 18 parts of Captex® 355 caprylic/capric triglyceride from ABITEC Corporation (fragrance diluent). Thereafter, the designated amount (in parts by weight) of the various isocyanates were added to the reactor under agitation by a mixer blade. Once adequately mixed, the agitation mixer blade was paused and replaced with a milling blade. The water phase was then added to the reactor gradually under high shear milling: the high shear milling maintained until the targeted emulsion droplet size of around 25 microns was attained. Once the target emulsion droplet size was achieved, milling was paused, and the milling blade switched out for the mixer blade to keep the emulsion mixed. Thereafter, the temperature of the reactor vessel was raised from ambient to 50° C. over a period of 60 min, and the temperature maintained at 50° C. for an additional 60 min. Subsequently, the temperature was then raised to 65° C. over 60 min, and maintained at 65° C. for an additional 120 min. Thereafter, the temperature was raised to 85° C. over a period of 60 min, and maintained at 85° C. for an additional four hours, at which time the process was deemed complete. The resulting microcapsule slurries in the reactor was allowed to cool to ambient temperature. The slurries were found to be of low viscosity and generally uniform and smooth with no visible thickening and/or agglomeration.

The microcapsules were subjected to leakage testing in heavy duty laundry cleaner and liquid fabric enhancer, as discussed above. The results are presented in Table 2. As evident from these results one is able to fine tune the release properties/characteristics of the microcapsules based on the selection of the isocyanate, the combination of isocyanates and the relative ratios of each. Particularly surprising was the finding that excellent leakage prevention is attained by employing combinations of isocyanates, irrespective of whether one is aliphatic, aromatic or cycloaliphatic, particularly where the aliphatic isocyanate is present in an amount of at least 25%, preferably about 50% or more, preferably less than 95%, more preferably less than 90%.

TABLE 2

| | Isocyanates | | | | | Leakage, one week @ 35° C. | |
|---|---|---|---|---|---|---|---|
| Example | Takenate D110N | Mondur MR Light | Desmodur W | Desmodur N3200A | % Takenate | | |
| 24 | 5.00 | 0.00 | | | 100 | 76.31 | 37.47 |
| 25 | 3.75 | 1.25 | | | 75 | 16.66 | 10.65 |
| 26 | 2.50 | 2.50 | | | 50 | 26.30 | 21.38 |
| 27 | 0.00 | 5.00 | | | 0 | 81.84 | 37.60 |
| 28 | 3.75 | | 1.25 | | 75 | 19.62 | 11.75 |
| 29 | 2.50 | | 2.50 | | 50 | 42.12 | 23.48 |
| 30 | 0.00 | | 5.00 | | 0 | 96.16 | 50.78 |
| 31 | 3.75 | | | 1.25 | 75 | 10.74 | 5.73 |
| 32 | 2.50 | | | 2.50 | 50 | 13.54 | 9.49 |
| 33 | 0.00 | | | 5.00 | 0 | 88.82 | 51.40 |

Although the process and prepared microcapsules of the present specification have been described with respect to specific embodiments and examples, it should be appreciated that the present teachings are not limited thereto and other embodiments utilizing the concepts expressed herein are intended and contemplated without departing from the scope of the present teaching. Thus, the true scope of the present teachings is defined by the claimed process steps and any and all modifications, variations, or equivalents that fall within the spirit and scope of the underlying principles set forth herein.

I claim:

1. Microcapsules having a shell wall comprising urethane and/or urea linkages and isocyanate and/or bis- or poly-chloroformate segments and polypeptide segments, the polypeptide segments having an average molecular weight of from at least 1000 Da to less than 10,000 Da and the weight ratio of the isocyanate and/or bis- or poly-chloroformate segments to the polypeptide segments being from 100:1 to 1:100.

2. The microcapsules of claim 1 wherein the shell wall comprises isocyanate segments and polypeptide segments wherein the polypeptide segments have an average molecular weight of from 1700 Da to 7,000 Da and the weight ratio of the isocyanate and/or his- or poly-chloroformate segments to the polypeptide segments being from 10:1 to 1:10.

3. The microcapsules of claim 1 wherein the shell wall comprises isocyanate segments and polypeptide segments wherein the polypeptide segments have an average molecular weight of from 1700 Da to 5,500 Da and the weight ratio of the isocyanate and/or bis- or poly-chloroformate segments to the polypeptide segments being from 1:5 to 1:0.2.

4. The microcapsules of claim 1 wherein the polypeptide segments comprise from 5 to 50 amino acids.

5. The microcapsules of claim 1 wherein the polypeptide segments comprise from 15 to 45 amino acids.

6. The microcapsules of claim 1 further comprising cross-link segments, the cross-link segments derived from compounds, dimers, oligomers, and low molecular weight polymers having two to five, primary or secondary amine groups or hydroxy groups or a combination of hydroxy and amine groups.

7. The microcapsules of claim 1 wherein the isocyanate is an aromatic isocyanate.

8. The microcapsules of claim 1 wherein the isocyanate is an aliphatic or cycloaliphatic isocyanate.

9. The microcapsules of claim 1 wherein the isocyanate is a combination of aliphatic isocyanates, cycloaliphatic isocyanates and/or aromatic isocyanates.

10. The microcapsules of claim 9 wherein the isocyanate is a combination of an aromatic isocyanate and an aliphatic and/or cycloaliphatic isocyanate.

11. The microcapsules of claim 9 wherein the isocyanate is a combination of an aliphatic isocyanate and another aliphatic or a cycloaliphatic isocyanate.

12. The microcapsules of claim 9 wherein each isocyanate is present in an amount of 5-95 weight percent.

13. Microcapsules whose shell wall comprises the reaction product of polypeptides having an average molecular weight of from at least 1000 Da to less than 10,000 Da with isocyanates and/or bis- or poly-chloroformates, wherein the weight ratio of the isocyanate and/or bis or poly-chloroformate reactants to the polypeptides reactants is from 100:1 to 1:100.

14. The microcapsules of claim 13 comprising the reaction products of isocyanates wherein isocyanates have 2 to 4 isocyanate groups and the polypeptides having at least two sites reactive with the isocyanates.

15. The microcapsules of claim 13 wherein the polypeptides have an average molecular weight of from 1700 Da to 7,000 Da and the weight ratio of the isocyanates to the polypeptides is from 10:1 to 1:10.

16. The microcapsules of claim 13 wherein the polypeptides segments have an average molecular weight of from 1700 Da to 5,500 Da and the weight ratio of the isocyanates to the polypeptides is from 1:5 to 1:0.2.

17. The microcapsules of claim 13 wherein the polypeptide segments comprise from 5 to 50 amino acids.

18. The microcapsules of claim 1 wherein the polypeptide segments comprise from 15 to 45 amino acids.

19. The microcapsules of claim 13 wherein the wall forming reactants further include one or more compounds, dimers oligomers and low molecular weight polymers having two to five, primary or secondary amine groups or hydroxy groups or a combination of hydroxy and amine groups.

20. The microcapsules of claim 13 wherein the isocyanate is a combination of aliphatic isocyanates, cycloaliphatic isocyanates and/or aromatic isocyanates.

21. An article of manufacture incorporating the microcapsules according to claim 1.

22. The article of manufacture according to claim 21, wherein the article is selected from the group consisting of a soap, a surface cleaner, a laundry detergent, a fabric softener, a shampoo, a textile, a paper towel, an adhesive, a wipe, a diaper, a feminine hygiene product, a facial tissue, a pharmaceutical, a napkin, a deodorant, a heat sink, a foam, a pillow, a mattress, bedding, a cushion, a cosmetic, a medical device, packaging, an agricultural product, a cooling fluid, a wallboard, and insulation.

* * * * *